(12) United States Patent
Neumeier et al.

(10) Patent No.: US 12,145,951 B2
(45) Date of Patent: Nov. 19, 2024

(54) INORGANIC-ORGANIC HYBRID COMPOUNDS INCLUDING ORGANIC PLATINUM-CONTAINING ANIONS, FOR USE IN MEDICINE

(71) Applicants: Karlsruher Institut fur Technologie, Karlsruhe (DE); Max-Planck-Gesellschaft zur Forderung der Wissenschaften e.V., Munich (DE)

(72) Inventors: Beatrice Lilli Neumeier, Rauenberg (DE); Claus Feldmann, Ettlingen (DE); Joanna Napp, Rosdorf (DE); Frauke Alves, Gottingen (DE)

(73) Assignees: Karlsruher Institut fur Technologie (DE); Max-Planck-Gesellschaft zur Forderung der Wissenschaften e.V. (DE)

( * ) Notice: Subject to any disclaimer, the term of this patent is extended or adjusted under 35 U.S.C. 154(b) by 826 days.

(21) Appl. No.: 17/263,600

(22) PCT Filed: Jul. 26, 2019

(86) PCT No.: PCT/EP2019/070220
§ 371 (c)(1),
(2) Date: Jan. 27, 2021

(87) PCT Pub. No.: WO2020/025488
PCT Pub. Date: Feb. 6, 2020

(65) Prior Publication Data
US 2021/0292353 A1    Sep. 23, 2021

(30) Foreign Application Priority Data
Jul. 30, 2018 (EP) .............................. 102018006012

(51) Int. Cl.
| | | |
|---|---|---|
| *C07F 15/00* | (2006.01) | |
| *A61K 33/243* | (2019.01) | |
| *B82Y 5/00* | (2011.01) | |
| *B82Y 30/00* | (2011.01) | |
| *B82Y 40/00* | (2011.01) | |

(52) U.S. Cl.
CPC ........ *C07F 15/0086* (2013.01); *A61K 33/243* (2019.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

2017/0112948 A1 * 4/2017 Heck .................. C07F 9/301
2017/0151350 A1 * 6/2017 Omary .................. C09K 11/06

FOREIGN PATENT DOCUMENTS

WO    2017213494    12/2017

OTHER PUBLICATIONS

Talal, A.K., et al., Heterobimetallic complexes of platinum(II) with diferrocenylphenylphosphine and their in vitro activity against P3888 leukaemia, Applied Organometallic Chem., 13, 63-68 (1999); (Year: 1999).*
Rice, S.F., & Gray, H.B., Electronic Absorption and Emission Spectra of Binuclear Platinum(II) Complexes. Characterization of the Lowest Singlet and Triplet Excited States of Pt2(H2P2O5)44-, J. Am. Chem. Soc. 1983, 105, 4571-4575 (Year: 1983).*
Patent Cooperation Treaty (PCT), International Search Report and Written Opinion for Application PCT/EP2019/070220 filed on Jul. 26, 2019, mailed Oct. 2, 2019, International Searching Authority, EP.
Talal et al., "Heterobimetallic Complexes of Platinum (II) with Diferrocenylphosphine and their in Vitro Activity Against P388 Leukaemia Introduction," Applied Organometallic Chemistry, 1999. Vol. 13, pp. 63-6368.
Rice et al., Electronic absorption and emission spectra of binuclear platinum (II) complexes. Characterization of the Lowest Singlet and Triplet Excited States of Pt2(H2p2o5)44. 1983. vol. 105. pp. 4571-4575.

* cited by examiner

*Primary Examiner* — H. Sarah Park
(74) *Attorney, Agent, or Firm* — McDonald Hopkins LLC

(57) ABSTRACT

The present invention relates to inorganic-organic hybrid compounds for use in medicine or for use as medication, consisting of an inorganic metal cation and an organic platinum-containing cytostatic anion, in particular also a cisplatin derivative.

9 Claims, 4 Drawing Sheets

Figure 1:
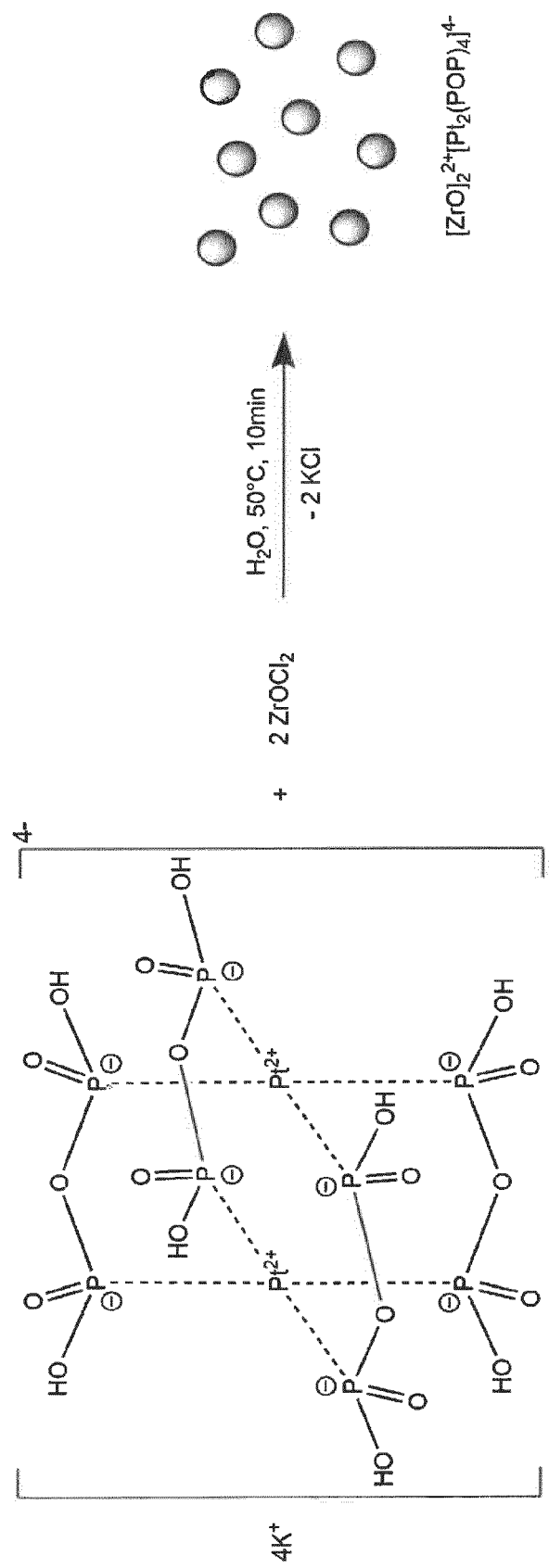

INORGANIC-ORGANIC HYBRID COMPOUNDS INCLUDING ORGANIC PLATINUM-CONTAINING ANIONS, FOR USE IN MEDICINE

CROSS-REFERENCE TO RELATED APPLICATION

This application is a 35 U.S.C. 371 national stage filing of PCT Application No. PCT/EP2019/070220 filed on Jul. 26, 2019, entitled "INORGANIC-ORGANIC HYBRID COMPOUNDS INCLUDING ORGANIC PLATINUM-CONTAINING ANIONS, FOR USE IN MEDICINE," which claims priority to German Patent Application No. 102018006012.9, filed on Jul. 30, 2018, each of which are incorporated herein in their entirety by reference.

The present invention relates to inorganic-organic hybrid compounds for use in medicine or for use as medication, consisting of an inorganic metal cation and an organic platinum-containing cytostatic anion, in particular also a cisplatin derivative.

The targeted release of pharmaceuticals (drug delivery) with nanoparticles represents a major challenge for interdisciplinary sciences of this time. Currently, a large number of different material and therapy concepts is being pursued for a wide variety of diseases. The encapsulation of active ingredients in vesicles, meso- or nanoscale hollow spheres or polymer capsules is widespread. In addition, active ingredients are bound to nanoparticles such as $SiO_2$, Au, quantum dots or polymer nanoparticles.

Alternatively, active ingredients can also be embedded in nanoparticles, with $SiO_2$ and polymers being the most common matrix materials. Disadvantages of the currently discussed materials and solution approaches are the sometimes very small amount of active ingredient in relation to the nanoparticles as a whole (e.g. 1% active ingredient encapsulated in 99% $SiO_2$ as a nanoparticle matrix), the incomplete degradability or potential toxicity of the nanoparticles after release of the active ingredient ($SiO_2$ nanoparticles remain, for example). In addition, the material concepts and the synthesis of the materials are complex and very time-consuming. This is particularly the case for multifunctional nanoparticles, which, in addition to the release of active ingredients, also enable analytical detection.

In summary, the following points can be listed as disadvantages of drug delivery systems and materials according to the prior art:
- complex chemical synthesis, multi-stage processes;
- complex material systems such as core-shell structures and complex modification of the particle surface;
- small amount of active ingredient based on the total mass of the nanoparticles;
- toxic components or components that are not completely or only very slowly degradable/excretable under physiological conditions;
- effectiveness of a complex material system only against one disease;
- active ingredient bound to a nanoparticle only superficially and therefore easily rubbed off in suspension by impact of particle;
- occurrence of significant side effects; too fast or too slow a release of the respective pharmaceuticals.

The targeted release of platinum derivatives, especially cisplatin derivatives, is a particularly great challenge. Cisplatin derivatives are generally among the most effective and widely used cytostatics, with the following significant disadvantages though:
- unspecific and unselective uptake, so that especially all rapidly growing cells are affected,
- significant side effects that are favored by the unspecific/unselective uptake,
- cisplatin derivatives are used almost exclusively in dissolved form,
- so far, nanoparticles contain only small amounts of cisplatin based on the total mass of the nanoparticles (i.e. <5% by weight),
- no platinum-containing anions with phosphate, phosphonate, sulfonate or carboxylate groups are present, which are essential for the poor solubility in water and the formation of nanoparticles in water.

Against this background, it is the object of the present invention to provide a simple material concept with—at the same time—a very wide range of applications on the basis of corresponding platinum derivatives, in particular cisplatin derivatives, for use in medicine.

This object is solved by the embodiments characterized in the claims.

In particular, inorganic-organic hybrid compounds for use in medicine, made up as ionic compounds from an inorganic metal cation selected from $Ba^{2+}$, $[ZrO]^{2+}$, $[HfO]^{2+}$, $Sc^{3+}$, $Y^{3+}$, $Gd^{3+}$, $[GdO]^+$, $[Gd(OH)]^{2+}$, $[LaO]^+$, $[La(OH)]^{2+}$, $Fe^{3+}$, $Bi^{3+}$, $Ag^+$ or a lanthanide and an organic platinum-containing anion containing at least one phosphate, pyrophosphate, phosphonate, sulfate, sulfonate, carbonate or carboxylate group as a functional group, wherein the compound has a molar solubility of $\leq 10^{-2}$ mol/l in water and a particle diameter in the range from 1 to 100 nm, are provided. The present invention thus relates to pharmaceutical compositions comprising at least one such inorganic-organic hybrid compound.

In a preferred embodiment of the present invention, the metal cation is selected from $Ba^{2+}$, $[ZrO]^{2+}$, $[HfO]^{2+}$, $[GdO]^+$, $[Gd(OH)]^{2+}$, $[LaO]^+$, $[La(OH)]^{2+}$ or $Ag^+$.

The organic platinum-containing anion preferably contains at least one phosphate, pyrophosphate or phosphonate group as a functional group. Particularly preferably, the organic platinum-containing anion is selected from one of the following:
- $[Pt_2(POP)_4]$ (POP: pyrophosphate),
- $[cisPt(AEP)_2]^{4-}$ (AEP: aminoethyl phosphate), or
- $[cisPt(PAA)_2]^{4-}$ (PAA: phosphonoacetate).

In order to make platinum derivatives, in particular also cisplatin derivatives, available for the concept of the inorganic-organic hybrid nanoparticles according to the invention at all, a corresponding modification of platinum derivatives, in particular cisplatinum derivatives, with phosphate, pyrophosphate, phosphonate, sulfate, sulfonate, carbonate or carboxylate groups is required. This modification is extremely complex. The platinum-containing anions listed above are new and not commercially available.

The inorganic-organic hybrid nanoparticles according to the invention turn out to be very promising alternatives to classic platinum derivatives, in particular cisplatinum derivatives. Advantages of these inorganic-organic hybrid compounds in the form of nanoparticles are the high cell uptake, the high effectiveness, the low side effects, and the possibility of combining several cytostatics in one nanoparticle as well as the multimodal detection via optical and magnetic imaging methods.

In particular, the inorganic-organic hybrid nanoparticles according to the invention are free from corresponding matrices or encapsulations surrounding them, in particular for example an $SiO_2$ matrix, and free from any phospholipid matrices or encapsulations.

In one embodiment of the present invention, the inorganic-organic hybrid compounds can furthermore comprise a fluorescence dye anion and/or an active ingredient anion, which each carry a phosphate, phosphonate, sulfate, sulfonate, carbonate or carboxylate group as a functional group, so that the inorganic-organic hybrid compound can release an active ingredient and/or can be localized in cells, tissue, organs by light emission due to the fluorescence of the fluorescence dye anion. The platinum-containing anion compulsory in the inorganic-organic hybrid compounds according to the invention, may, however, itself function as an active ingredient, for example with cytostatic properties, or as a fluorescence dye due to its fluorescence.

In addition to the organic platinum-containing cytostatic anion, its release and the resulting cytostatic effect, the inorganic-organic hybrid nanoparticles according to the invention can contain several cytostatic anions or other active ingredient anions as well as fluorescence dye anions. Fluorescent dye anions enable both optical and/or photoacoustic imaging. As already stated above, the platinum-containing anion itself can also have fluorescence in individual cases.

"Active ingredient anion" is understood to mean a substance that is designated as an agent for curing or preventing human or animal diseases, as well as a substance that is intended for use in or on the human or animal body to make a medical diagnosis or to restore, improve or influence human or animal body functions.

The organic active ingredient anion possibly additionally incorporated into the inorganic-organic hybrid compound according to the invention is not subject to any significant restriction, as long as it contains at least one phosphate, phosphonate, sulfate, sulfonate, carbonate or carboxylate group, preferably phosphate, phosphonate, sulfate or sulfonate group, as a functional group which, in conjunction with the inorganic cation, enable the formation of a compound that is poorly soluble in water and thus enables the formation of nanoparticles. Such active ingredients are known to the skilled person. In the context of the present invention, use can be made e.g. of acetaminophen phosphate, betamethasone phosphate, dexamethasone phosphate, uridine monophosphate, 5'-fluoro-2'-deoxyuridine-5'-monophosphate (FdUMP), methylprednisolone phosphate, triamcinolone phosphate, estrone phosphate, testosterone phosphate, estramustine phosphate, codeine phosphate, clindamycin phosphate, thiamine pyrophosphate, thiamine phosphate; aracytidinmonophosphat, cyclic-3',5'adenosine monophosphate, vidaribine phosphate, 9-[9-(phosphonomethoxy)ethoxy]adenine, fospropofol, fosphenytoin, phosphoryloxymethyloxymethylphenytoin, phosphoryloxymethylphenylbutazone, phosphoryloxymethyloxymethylphenylbutazone, phosphoryloxymethylphenindione, phosphoryloxymethyloxymethylphenindione, N-phosphonooxymethylcinnarizine, N-phosphonooxymethylloxapine, N-phosphonooxymethylamiodarone, alendronate, canrenoate, doxycycline hydrate, doxorubicin hydrochloride, aztreonam, tigemonam, D-glucosamine-6-sulphate, colistin methanesulphate, cefsulodin, fosamprenavir, tenofovir, adefovir, combretastatin A-4 phosphate, folic acid, fosphenytoin, 2-mercaptoethanesulfonate/mesna, fosfomycin, glyphosate, glufosinate, zolendronate, aminotrimethylene phosphonic acid, diethylenetriamine penta(methylene phosphonic acid), ethylenediamine tetra(methylene phosphonic acid), fosbretabulin, $\alpha$-tocopherol phosphate, VAPOL hydrogenphosphate, pyridoxal-5'-phosphate-6-(2'-naphthylazo-6'-nitro-4',8'-disulfonate), (11 bR)-2,6-di-9-phenanthrenyl-4-hydroxy-dinaphtho[2,1-d:1',2'-f] [1,3,2]dioxaphosphepine-4-oxide, 8-bromo-cyclic adenosine diphosphate ribose, phytic acid, glucose-6-phosphate or other phosphoric acid esters of sugars or naturally occurring and synthetic nucleotides (e.g. adenosine monophosphate (AMP), adenosine diphosphate (ADP), adenosine triphosphate (ATP), guanosine monophosphate (GMP), guanosine diphosphate (GDP), guanosine triphosphate (GTP), cytidine monophosphate (CMP), cytidine diphosphate (CDP), cytidine 20 triphosphate (CTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxycytidine monophosphate (dCMP), deoxycytidine diphosphate (dCDP), deoxycytidine triphosphate (dCTP), deoxythymidine monophosphate (dTMP), deoxythymidine diphosphate (dTDP) deoxythymidin triphosphate (dTTP). In addition, organic active ingredients can also be used, which as such do not have any phosphate, phosphonate, sulfate, sulfonate, carbonate or carboxylate group, by modifying them with at least one of these functional groups. Corresponding methods for the functionalization of such organic active ingredients are known to the skilled person.

Particularly preferably, the additionally incorporated organic active ingredient anion is selected from: acetaminophen phosphate, betamethasone phosphate, dexamethasone phosphate, 5'-fluoro-2'-deoxyuridine-5'-monophosphate (FdUMP), methyl prednisolone phosphate, triamcinolone phosphate, estrone phosphate, estramustine phosphate, codeine phosphate, clindamycin phosphate, fospropofol, alendronate, canrenoate, doxycycline hydrate, doxorubicin, aztreonam, tigemonam, cefsulodin, fosamprenavir, tenofovir, adefovir, folic acid, fosfomycin, $\alpha$-tocopherol phosphate or glucose-6-phosphate.

The inorganic-organic hybrid compound according to the invention can also be understood to comprise an inorganic matrix and an organic platinum-containing compound, the inorganic matrix being composed of an inorganic compound selected from the group consisting of metal phosphates, including the pyrophosphates, hydrogen phosphates and dihydrogen phosphates, metal oxide phosphates, metal phosphonates, metal sulfates, metal sulfonates, metal carbonates or metal carboxylates, the inorganic compound including a cation selected from $Ba^{2+}$, $[ZrO]^{2+}$, $[HfO]^{2+}$, $Sc^{3+}$, $Y^{3+}$, $Gd^{3+}$, $[GdO]^+$, $[Gd(OH)]^{2+}$, $[LaO]^+$, $[La(OH)]^{2+}$, $Fe^{3+}$, $Bi^{3+}$, $Ag^+$ or a lanthanide, the organic platinum-containing anion (organic platinum-containing compound) having one or more functional groups selected from phosphate, pyrophosphate, phosphonate, sulfate, sulfonate, carbonate or carboxylate groups, via which the platinum unit is incorporated into the inorganic matrix. Insofar as the platinum compound (as well as the optional active ingredient compound and/or the optional fluorescence dye) is incorporated into the inorganic matrix via its functional group by means of ionic bonding, the functional group, e.g. phosphate, is accordingly to be assigned to the inorganic matrix, i.e. there is no independent phosphate group on the platinum compound.

In addition to the organic platinum-containing anion, hydrogen phosphate can also be present as an anion (e.g. $[ZrO]^{2+}{}_2[(cisPt(AEP)_2)_{0.5}(HPO_4)_{1.0}]^{4-})$.

In a preferred embodiment of the present invention, the inorganic-organic hybrid compound, as already stated above, optionally contains an organic fluorescence dye, i.e. a corresponding anion thereof, which has one or more functional groups selected from phosphate, phosphonate, sulfate, sulfonate, carbonate or carboxylate groups, via which the fluorescence dye (anion) is incorporated into the ionic compound or inorganic matrix. The organic fluorescence dye is preferably selected from the group consisting of 1,1'-diethyl-2,2'-cyanine iodide, 1,2-diphenylacetylene, 1,4-diphenylbutadiene, 1,6-diphenylhexatriene, 2,5-diphenyloxazole, 2-methylbenzoxazole, 4',6-diamidino-2-phenylindole (DAPI), 4-(dicyanomethylene)-2-methyl-6-(p-dimethylaminostyryl)-4H-pyrane (DCM), 4-dimethylamino-4'-nitrostilbene, 5,10,15-triphenylcorrole, 5,10,15-tris (pentafluorophenyl)corrole, 5,10-diarylchlorin, 5,10-diarylcopper chlorin, 5,10-diarylcopper oxochlorin, 5,10-diarylmagnesium oxochlorin, 5,10-diaryloxochlorin, 5,10-diarylzinc chlorin, 5,10-diarylzinc oxochlorin, 7-benzylamino-4-nitrobenz-2-oxa-1,3-diazole, 7-methoxycoumarin-4-acetic acid, 9,10-bis(phenylethynyl)anthracene, 9,10-diphenylanthracene, acridine orange, acridine yellow, adenine, anthracene, anthraquinone, auramine O, azobenzene, Bacteriochlorophyll A, benzoquinone, beta-carotene, bilirubin, biliverdin dimethyl ester, bis(5-mesyldipyrrinato) zinc, bis(5-phenyldipyrrinato)zinc, boron subphtalocyanine chloride, chlorin E6, chlorophyll A, chlorophyll B, cis-stilbene, coumarin and derivatives thereof, cresyl violet perchlorate, cryptocyanine, crystal violet, cytosine, dansylglycine, diprotonated-tetraphenylporphyrin, eosin and derivatives thereof, ethyl-(p-dimethylamino)benzoate, ferrocene, fluorescein and derivatives thereof, for example methylfluorescein, resorufin, amaranth, aluminum(III)-phthalocyanine chloride, tetrasulfonic acid, trypan blue, guanine, hematine, histidine, Hoechst 33258, indocarbocyanine and derivatives thereof, Lucifer yellow CH, magnesium octaethylporphyrin, magnesium phthalocyanine, magnesium tetramesitylporphyrin, magnesium tetraphenylporphyrin, malachite green, merocyanine, N,N'-difluoroboryl-1,9-dimethyl-5-(4-iodophenyl)-dipyrrin, N,N'-difluoroboryl-1,9-dimethyl-5-[(4-(2-trimethylsilylethynyl)phenyl]dipyrrin, N,N'-difluoroboryl-1,9-dimethyl-5-phenydipyrrin, tetraphenylporphyrin, naphthalene, Nile Blue, Nile Red, octaethylporphyrin, oxacarbocyanine and derivatives thereof, oxazine and derivatives thereof, p-quarterphenyl, p-terphenyl, perylene and derivatives thereof, phenol, phenylalanine, phenyldipyrrin, pheophorbide, phthalocyanine, pinacyanol iodide, piroxicam, porphine, proflavine, protoporphyrin-IX-dimethyl ester, pyrene, pyropheophorbide and derivatives thereof, pyrrole, quinine, rhodamine and derivatives thereof, riboflavin, Bengal red, squarylium dye III, TBP-beta-octa (COOBu)-Fb, TBP-beta-octa(COOBu)-Pd, TBP-beta-octa (COOBu)-Zn, TBP-meso-tetraphenyl-beta-octa(COOMe)-Fb, TBP-meso-tetraphenyl-beta-octa(COOMe)-Pd, TBP-meso-tetraphenyl-beta-octa(COOMe)-Zn, TCPH-meso-tetra(4-COOMe-phenyl)-Fb, TCPH-meso-tetra(4-COOMe-phenyl)-Pd, TCPH-meso-tetra(4-COOMe-phenyl)-Zn, tetra-t-butylazaporphine, tetra-t-butylnaphthalocyanine, tetrakis (2,6-dichlorophenyl)porphyrin, tetrakis(o-aminophenyl) porphyrin, tetramesityl porphyrin, tetraphenylporphyrin, tetraphenylsapphyrin, thiacarbocyanine and derivatives thereof, thymine, trans-stilbene, tris(2,2'-bipyridyl)ruthenium(II), tryptophan, tyrosine, uracil, vitamin B12, zinc octaethylporphyrin, phthalocyanine and derivatives thereof, porphyrin and derivatives thereof, e.g. tetra(o-amidophosphonophenyl)porphyrin, and umbelliferone. Here, the organic fluorescence dyes, which as such do not have a phosphate, phosphonate, sulfate, sulfonate, carbonate or carboxylate group, are modified with at least one of these functional groups (e.g. phenylumbelliferone phosphate (PUP), methylfluorescein phosphate (MFP), resorufin phosphate (RRP), Dyomics-647-uridine phosphate (DUT)). Corresponding methods for functionalizing such organic fluorescence dyes are known to the skilled person.

In the context of the present invention, it is possible to carry out the detection of the inorganic-organic hybrid compounds according to the invention not only optically via the fluorescence of an optionally incorporated fluorescence dye anion, but in the presence of heavy or magnetic inorganic cations (e.g. $Ba^{2+}$, $[ZrO]^{2+}$, $[HfO]^{2+}$, $Gd^{3+}$, $La^{3+}$, $Fe^{3+}$, $Bi^{3+}$) also by X-ray absorption or magnetic measurements. For example, if paramagnetic cations such as $Gd^{3+}$ are used, magnetic imaging is possible as well.

In a further embodiment of the present invention, the inorganic-organic hybrid compound is further functionalized with one or more tumor-specific ligands (e.g. small organic molecules, peptides, antibodies and nucleic acids) in order to e.g. specifically target cancer cells by selective binding to tumor-specific surface-expressed receptors or to bring the inorganic-organic hybrid nanoparticles and the active ingredient contained therein to a specific site of action and to enrich them there. Due to the water-based synthesis of the inorganic-organic hybrid compounds, this coupling with antibodies or similar molecules is particularly easy and gentle.

The inorganic-organic hybrid compounds according to the invention are poorly soluble. In the context of the present invention, poorly soluble compounds are understood to mean those compounds that have a molar solubility of ≤10-2 mol/l. The poorly soluble compounds preferably have a molar solubility of ≤10-4 mol/l. This is advantageous with regard to the synthesis of the inorganic-organic hybrid compounds according to the invention, since in this way the inorganic-organic hybrid compound that contains the platinum-containing anion can be precipitated from soluble precursor compounds.

The inorganic-organic hybrid compound usually has an X-ray amorphous structure. This is advantageous with regard to a simplified synthesis, since amorphous nanoparticles can be obtained without major synthetic effort.

Optionally, the inorganic-organic hybrid compound can be further doped with one or more cations and/or anions. Such doping makes it possible to modify the luminescence properties of the hybrid compound according to the invention, since after excitation of a fluorescence dye, if present, a complete or partial energy transfer to the doping takes place, so that an emission originating from the doping can be observed afterward. It is furthermore possible that the doping effects a changed excitation of the hybrid compound according to the invention. The doping can take place in any suitable concentration range. The doping is preferably present in a concentration range from 5 ppm to 50 mol %, particularly preferably in a concentration range from 0.1 to 5.0 mol %. If the inorganic metal cation is not a lanthanide, the inorganic-organic hybrid compound is preferably doped with a lanthanide selected from La, Ce, Pr, Nd, Sm, Eu, Gd, Tb, Dy, Ho, Er, Tm, Yb or Lu, a transition metal selected from Cr, Mn, Cu, Zn, Y, Ag or Cd, a main group element selected from Sn, Sb, Pb or Bi, or a complex anion selected from $[VO_4]^{3-}$, $[MOO_4]^{3-}$ or $[WO_4]^{3-}$.

The hybrid compound according to the invention can have any suitable particle size. The hybrid compound according to the invention is usually nanoscaled and has a particle diameter in the range from 1 to 100 nm. A particle diameter in the range from 30 to 70 nm is particularly preferred. In addition, the hybrid compound according to the invention preferably has an almost monodisperse size distribution in the range of ±30%, particularly preferably in the range of ±5%. Moreover, the hybrid compound according to the invention preferably has a low degree of agglomeration, particularly preferably with a size distribution in the range of ±30%, even more preferably in the range of ±5%. In the prior art, suitable methods for determining the particle diameter and the monodisperse size distribution are known.

According to the present invention, different excitation and emission properties can be set with the same hybrid compound by the selection and incorporation of a corresponding organic fluorescence dye, if necessary. The excitation of the hybrid compound according to the invention is preferably in the range from 100 to 800 nm, and the emission in the range from 200 to 2000 nm. Usually, excitation is accomplished by a light-emitting diode or a laser, which emit visible to near-infrared light (i.e. 450 to 800 nm), and an emission of the organic fluorescence dye or the hybrid compound according to the invention in the visible spectral range between blue and infrared (i.e. 450 to 1400 nm). In another embodiment, the excitation takes place in the form of UV light (i.e. 100 to 450 nm). In the case of the hybrid compound according to the invention, the luminescence intensity under excitation conditions preferably decreases less strongly over the duration of the excitation compared to the unbound organic fluorescence dye, particularly preferably the luminescence intensity does not decrease over the duration of the excitation, in particular when excited with a light-emitting diode. Thus, upon exposure to UV light, the luminescence intensity preferably decreases by no more than 10%, and upon exposure to daylight by no more than 1%.

The present invention further relates to a method for producing the hybrid compounds according to the invention, comprising the steps of:
(a) providing a solution of a platinum-containing anion compound, which has one or more functional groups selected from phosphate, pyrophosphate, phosphonate, sulfate, sulfonate, carbonate or carboxylate groups,
(b) providing a solution of a soluble metal salt containing metal cations selected from $Ba^{2+}$, $[ZrO]^{2+}$, $[HfO]^{2+}$, $Sc^{3+}$, $Y^{3+}$, $Gd^{3+}$, $[GdO]^+$, $[Gd(OH)]^{2+}$, $[LaO]^+$, $[La(OH)]^{2+}$, $Fe^{3+}$, $Bi^{3+}$, $Ag^+$ or a lanthanide,
(c) combining the two solutions by stirring in order to precipitate the hybrid compound, and
(d) isolating and/or purifying the precipitated hybrid compound.

Step (a) of the method according to the invention comprises providing a solution of the organic platinum-containing anion. Furthermore, this solution can optionally further contain at least one anion selected from phosphate, phosphonate, sulfate, sulfonate, carbonate or carboxylate. If used, this anion can be present together with a cation in the form of a dissolved salt, for example as dissolved alkali metal sulfate, alkali metal phosphate, alkali metal carboxylate, alkali metal carbonate. Preferably, the alkali metal is sodium or potassium. The anion can also be present in the solution in the form of the corresponding acid.

In a preferred embodiment of the present invention, an organic active ingredient and/or an organic fluorescence dye, each of which has one or more functional groups selected from phosphate, phosphonate, sulfate, sulfonate, carbonate or carboxylate group, is added to the solution provided in step (a).

Any suitable solvent can be used as the solvent. Preferably, the solvent used is water, isotonic water, a physiological buffer, an alcohol or a mixture of several of these solvents. Preferred alcohols for use as solvents are methanol, ethanol, propanol and isopropanol.

Step (b) of the method according to the invention comprises providing a solution of a soluble metal salt containing metal cations that can be the same or different and are selected from $Ba^{2+}$, $[ZrO]^{2+}$, $[HfO]^{2+}$, $Sc^{3+}$, $Y^{3+}$, $Gd^{3+}$, $[GdO]^+$, $[Gd(OH)]^{2+}$, $[LaO]^+$, $[La(OH)]^{2+}$, $Fe^{3+}$, $Bi^{3+}$, $Ag^+$ or a lanthanide. Any suitable solvent can be used as the solvent. Preferably, the aforementioned solvents, namely water, isotonic water, a physiological buffer, alcohols and mixtures of several of these solvents are also used. In a particularly preferred embodiment of the present invention, isotonic water or a physiological buffer is used as the solvent. Any salt that is soluble in the solvent used can be used as the metal salt. Preferably, suitable metal salts are known to the skilled person. The halides, nitrates and sulfates of the aforementioned metals can be used as metal salts, provided that they are soluble in the particular solvent used.

Step (c) of the method according to the invention comprises combining the two solutions by stirring. In this way, the hybrid compound according to the invention is precipitated. In the step of combining, the two solutions can have any suitable temperature. In a preferred embodiment of the present invention, at least one of the two solutions or both solutions have a temperature in the range from room temperature to 85° C., particularly preferably a temperature in the range from 40° C. to 75° C. Combining of the two solutions is preferably done quickly, i.e. within a period of not more than 10 seconds, preferably within a period of not more than 5 seconds.

Step (d) of the method according to the invention comprises isolating and/or purifying the precipitated hybrid compound. This isolation and/or purification can be accomplished by any suitable method. Such methods are known in the prior art.

The hybrid compound particles are preferably isolated and/or purified by a method selected from the group consisting of centrifugation techniques, dialysis techniques, phase transfer techniques, chromatography techniques, ultrafiltration techniques, washing techniques and combinations thereof. The aforementioned methods for isolating and/or purifying the hybrid compound particles can also be combined and/or carried out several times.

Figure 2:
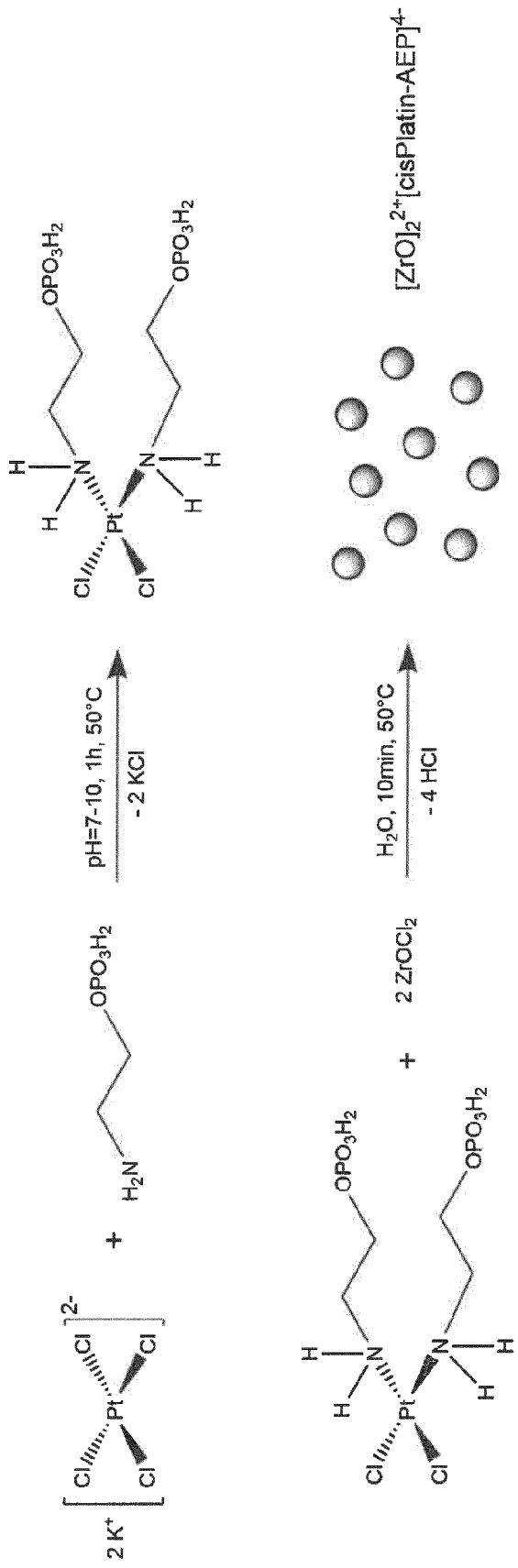
Figure 3:
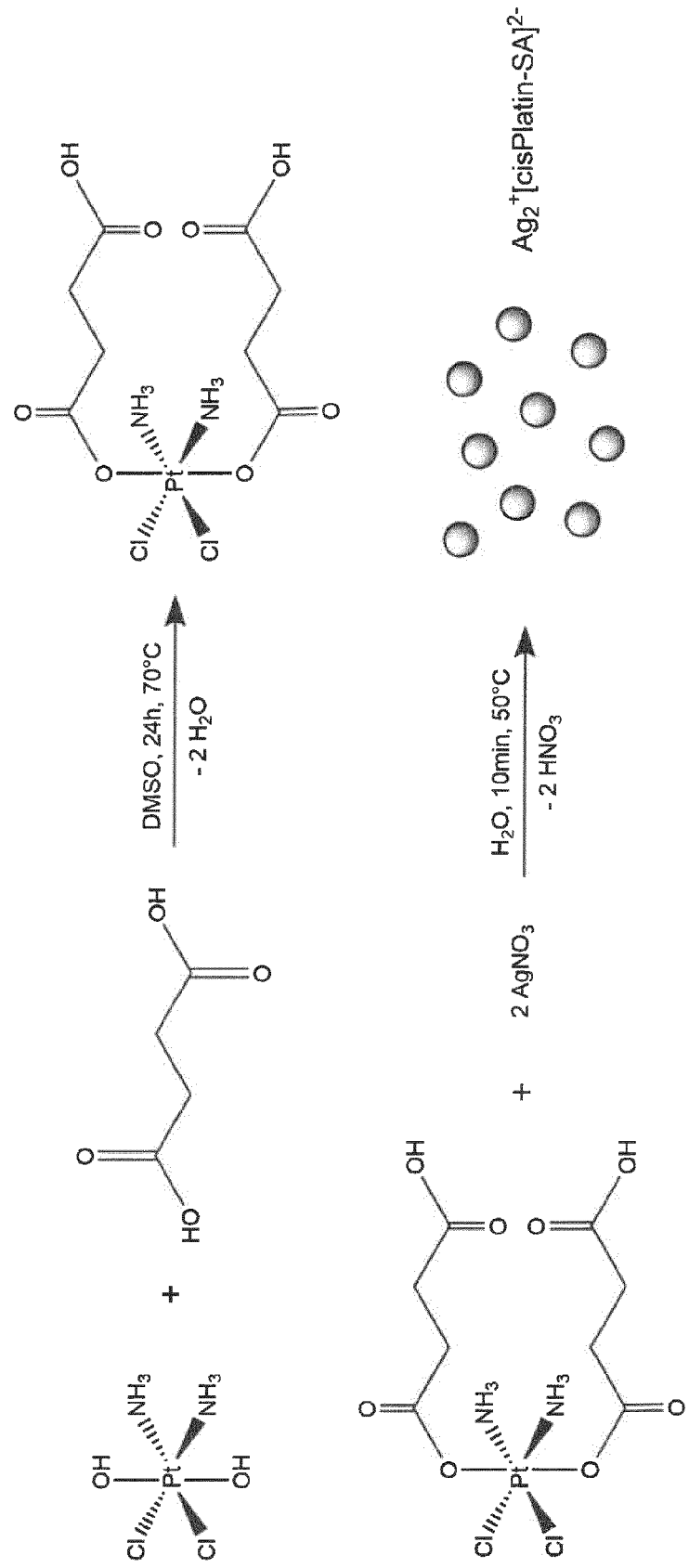
Figure 4:
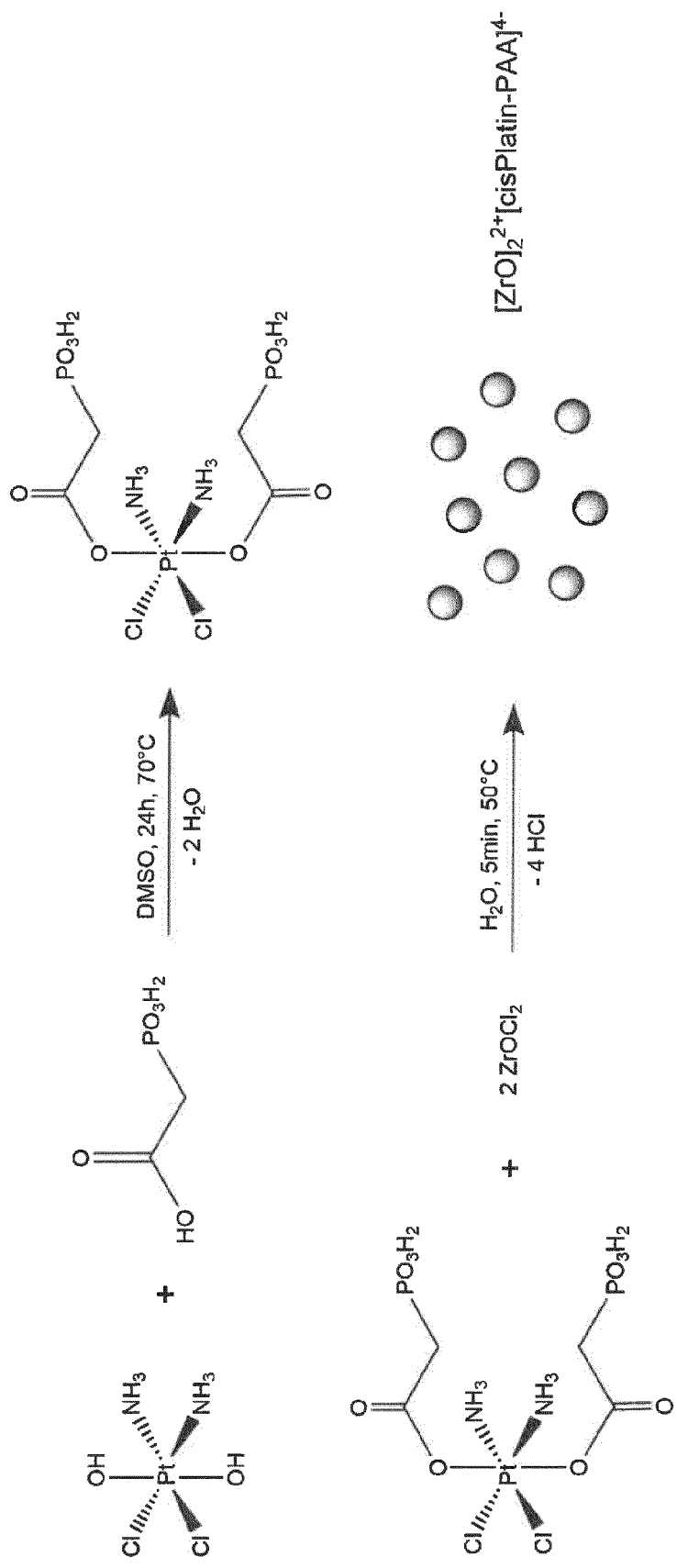

The figures show:
FIG. 1 the production of the inorganic-organic hybrid $[ZrO]_2^{2+}[Pt_2(POP)_4]^{4-}$,
FIG. 2 the production of the inorganic-organic hybrid $[ZrO]^{2+}{}_2[cisPt(AEP)_2]^{4-}$,
FIG. 3 the production of the inorganic-organic hybrid $[Ag]^+{}_2[cisPt(SA)_2]^{2-}$, and
FIG. 4 the production of the inorganic-organic hybrid $[ZrO]^{2+}{}_2[cisPt(PAA)_2]^{4-}$.

In summary, the present invention has the following advantages over the prior art:
- inorganic-organic hybrid nanoparticles with platinum-containing anions as a novel material concept with a novel chemical composition
- chemical composition with inorganic metal cations like $Ba^{2+}$, $[ZrO]^{2+}$, $[HfO]^{2+}$, $Sc^{3+}$, $Y^{3+}$, $Gd^{3+}$, $[GdO]^+$, $[Gd(OH)]^{2+}$, $[LaO]^+$, $[La(OH)]^{2+}$, $Fe^{3+}$, $Bi^{3+}$, $Ag^+$ or a lanthanide and a platinum-containing anion carrying phosphate, phosphonate, sulfate, sulfonate, carbonate or carboxylate groups
- high content of platinum-containing anions of 30 to 90% by weight
- high effectiveness and high uptake in cells with low side effects (compared to conventional cisplatin derivatives)

simple and inexpensive synthesis in water possibility of combining different active ingredient anions in one nanoparticle possibility of combining active ingredient anions and fluorescence dye anions multifunctional imaging including optical and/or photoacoustic and/or magnetic imaging synergistic tumor treatment through chemical/cytostatic and physical effects. Physical effects can be magnetothermal effects and/or photo-induced effects inorganic-organic hybrid nanoparticles are usually not crystalline (i.e., X-ray amorphous). The complex synthesis of crystalline materials or the formation of core-shell structures is not necessary selective uptake in tumors through EPR effect (Enhanced Permeability and Retention) through transport in macrophages and/or the attachment of suitable antibodies.

The present invention will be explained in further detail by the following non-limiting examples.

EXAMPLES

Embodiment 1: $[ZrO]_2^{2+}[Pt_2(POP)_4]^{4-}$

The inorganic-organic hybrid $[ZrO]_2^{2+}[Pt_2(POP)_4]$ (POP: pyrophosphate) is prepared by mixing two solutions. Solution 1 contains $ZrOCl_2 \times 8H_2O$ (6.5 mg) in demineralized water (5.0 ml). Solution 2 contains potassium pyrophosphatoplatinate(II) ($K_4[Pt_2(POP)_4]$), 20.3 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the yellow solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[ZrO]_2^{2+}[Pt_2(POP)_4]^{4-}$ (cf. FIG. 1), which contains $[ZrO]^{2+}$ as an inorganic cation and the cytostatic and green emitting anion $[Pt_2(POP)_4]^{4-}$, is obtained as amorphous nanoparticles with a diameter of about 40 nm.

Potassium pyrophosphatoplatinate ($K_4[Pt_2(POP)_4]$) (cf. FIG. 1) is produced according to a synthesis procedure known from the literature (cf. M. A. Filomena Dos Remedios Pinto, P. J. Sadler, S. Neidle, M. R. Sanderson, A. Subbiah, R. Kuroda, J. Chem. Soc.—Chem. Commun. 1980, 1, 13).

Embodiment 2: $[ZrO]^{2+}_2[cisPt(AEP)_2]^{4-}$

The inorganic-organic hybrid $[ZrO]^{2+}_2[cisPt(AEP)_2]^{4-}$ (AEP: aminoethyl phosphate) is prepared by mixing two solutions. Solution 1 contains $ZrOCl_2 \times 8H_2O$ (52 mg) in demineralized water (5.0 ml). Solution 2 contains potassium cis-dichloridodiaminoethylphosphatoplatinate(II) ($K_4[cisPt(AEP)_2]^{4-}$, 50.0 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the dark brown solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[ZrO]^{2+}_2[cisPt(AEP)_2]^{4-}$ (cf. FIG. 2), which contains $[ZrO]^{2+}$ as an inorganic cation and the cytostatic anion $[cisPt(AEP)_2]^{4-}$, is obtained as amorphous nanoparticles with a diameter of about 30 nm.

For the preparation of potassium cis-dichloridodiaminoethylphosphatoplatinate(II) ($K_4[cisPt(AEP)_2]^{4-}$, 50 mg of $K_2PtCl_4$ and 34 mg of aminoethyl phosphate (AEP) are dissolved in 10 mL water and the pH value is set to 7-10 using NaOH. The solution is heated to 50° C. for 60 min. Here, a color change from light orange to dark brown takes place. The brown product ($K_4[cisPt(AEP)_2]^{4-}$ (cf. FIG. 2) is then air-dried.

Embodiment 3: $[Ag]^+_2[cisPt(SA)_2]^{2-}$

The inorganic-organic hybrid $[Ag]^+_2[cisPt(SA)_2]^{2-}$ (SA: succinate) is prepared by mixing two solutions. Solution 1 contains $AgNO_3$ (12 mg) in demineralized water (0.3 ml). Solution 2 contains cis,cis,trans-diamminedichloridodisuccinatoplatinum(IV) (20.0 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the yellow solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[Ag]^+_2[cisPt(SA)_2]^{2-}$ (cf. FIG. 3), which contains $[Ag]^+$ as an inorganic cation and the cytostatic, orange-emitting anion $[cisPt(SA)_2]^{2-}$, is obtained as amorphous nanoparticles with a diameter of about 30 nm.

Synthesis of cis-diamminedichloridoplatinum(II) (cisplatin). Modified according to a synthesis known from the literature, 166 mg of $K_2PtCl_4$, 60 mg of KCl and 124 mg of $NH_4OAc$ are dissolved in 4 mL of water. The red-orange solution is heated in the microwave to 90° C. within one minute and kept at this temperature for a further 14 minutes. Subsequently, the reaction vessel (50 mL flask) is cooled in an ice bath and 16 mL of ethanol are added to completely precipitate the yellow-orange product. The precipitate is separated off by centrifugation (10 min, 15,000 $min^{-1}$). It is then extracted with 4 mL of DMF in order to separate off any platinum that may have formed (centrifugation, 10 min, 15000 $min^{-1}$). The product is precipitated from the yellow solution again with four times the amount of ethanol and purified by washing with ethanol twice. After drying, it is recrystallized in 0.1 M HCl at 90° C. The yellow-orange product cis-diamminedichloridoplatinum(II) (cf. FIG. 3) crystallizes out upon cooling, is centrifuged off, washed twice with ethanol and then dried.

Synthesis of cis,cis,trans-diamminedichloridodihydroxidoplatinum(IV) (cisplatinOH). Modified according to a synthesis known from the literature, 100 mg of cisplatin are suspended in 5 mL of water and an excess of 30% $H_2O_2$ (0.6 mL) is added. The mixture is stirred with stirring for 6 h at 70° C. and then overnight at room temperature. A color change from yellow-orange to light yellow takes place. The water is removed under vacuum, the light yellow product cis,cis,trans-diamminedichloridodihydroxidoplatinum(IV) (cf. FIG. 3) is purified by washing twice with ethanol and then dried.

Synthesis of cis,cis,trans-diamminedichloridodisuccinatoplatinum(V) (cisplatinSA). Modified according to a synthesis known from the literature, 100 mg (0.3 mmol) of cisplatinOH and 180 mg (1.8 mmol) of succinic anhydride are dissolved in 3 mL of DMSO and heated to 70° C. for 24 h with stirring. The solvent is then removed under vacuum and with heating to 50° C. Solvent residues are removed by repeatedly adding a few mL of water and then dry-drawing under vacuum. The yellow product cis,cis,trans-diamminedichloridodisuccinatoplatinum(IV) is washed with acetone and dried before further use (cf. FIG. 3).

Embodiment 4: $[ZrO]^{2+}{}_2[cisPt(PAA)_2]^{4-}$

The inorganic-organic hybrid $[ZrO]^{2+}{}_2[cisPt(PAA)_2]^{4-}$ (PAA: phosphonoacetate) is prepared by mixing two solutions. Solution 1 contains $ZrOCl_2 \times 8H_2O$ (21 mg) in demineralized water (0.3 ml). Solution 2 contains cis,cis,trans-diamminedichloridodiphosphonoacetatoplatinum(IV) (20.0 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the yellow solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[ZrO]^{2+}{}_2[cisPt(PAA)_2]^{4-}$ (cf. FIG. 4), which contains $[ZrO]^{2+}$ as an inorganic cation and the cytostatic, orange-emitting anion $[cisPt(PAA)_2]^{4-}$, is obtained as amorphous nanoparticles with a diameter of about 30 nm.

Synthesis of cis,cis,trans-diamminedichloridodiphosphonoacetatoplatinum(IV) (cisplatinumPAA). 100 mg of cisplatinOH and 168.0 mg of phosphonoacetic acid (PAA) are dissolved in 3 mL of DMSO and heated to 70° C. for 24 h while stirring. The solvent is then removed under vacuum and warming to 50° C. Solvent residues are removed by repeatedly adding a few mL of water and then dry-drawing under vacuum. The yellow product cis,cis,trans-diammindichloridodiphosphonoacetatoplatinum(IV) (cf. FIG. 4) is washed with acetone and dried before further use.

Embodiment 5: $[HfO]_2^{2+}[Pt_2(POP)_4]^{4-}$

The inorganic-organic hybrid $[HfO]_2^{2+}[Pt_2(POP)_4]^{4-}$ (POP: pyrophosphate) is prepared by mixing two solutions. Solution 1 contains $HfOCl_2 \times nH_2O$ (5.3 mg) in demineralized water (5.0 ml). Solution 2 contains potassium pyrophosphatoplatinate(II) ($K_4[Pt_2(POP)_4]$), 20.3 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the yellow solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[HfO]_2^{2+}[Pt_2(POP)_4]^{4-}$, which contains $[HfO]^{2+}$ as an inorganic cation and the cytostatic, green-emitting anion $[Pt_2(POP)_4]^{4-}$, is obtained as amorphous nanoparticles with a diameter of about 40 nm.

Potassium pyrophosphatoplatinate ($K_4[Pt_2(POP)_4]$) is produced according to a synthesis procedure known from the literature.

Embodiment 6: $[Gd(OH)]^{2+}[cisPt(SA)_2]^{2-}$

The inorganic-organic hybrid $[Gd(OH)]^{2+}[cisPt(SA)_2]^{2-}$ (SA: succinate) is prepared by mixing two solutions. Solution 1 contains $GdCl_3 \times 6H_2O$ (13 mg) in demineralized water (0.3 ml). Solution 2 contains cis,cis,trans-diamminedichloridodisuccinatoplatinum(IV) (20.0 mg) in demineralized water (50 ml). Solution 2 was heated to 50° C. and stirred powerfully (about 1000 $min^{-1}$). Solution 1 was then injected quickly with a syringe with intensive stirring. After stirring for two minutes, the colorless solid is separated off by centrifugation (15 min at 22,500 $min^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[Gd(OH)]^{2+}[cisPt(SA)_2]^{2-}$, which contains $[Gd(OH)]^{2+}$ as an inorganic cation and the cytostatic, orange-emitting anion $[cisPt(SA)_2]^{2-}$, is obtained as amorphous nanoparticles with a diameter of about 50 nm.

Synthesis of cis-diamminedichloridoplatinum(II) (cisplatin). Modified according to a synthesis known from the literature, 166 mg of $K_2PtCl_4$, 60 mg of KCl and 124 mg of $NH_4OAc$ are dissolved in 4 mL of water. The red-orange solution is heated in the microwave to 90° C. within one minute and kept at this temperature for a further 14 minutes.

Subsequently, the reaction vessel (50 mL flask) is cooled in an ice bath and 16 mL of ethanol are added to completely precipitate the yellow-orange product. The precipitate is separated off by centrifugation (10 min, 15,000 min$^{-1}$). It is then extracted with 4 mL of DMF in order to separate off any platinum that may have formed (centrifugation, 10 min, 15000 min$^{-1}$). The product is precipitated from the yellow solution again with four times the amount of ethanol and purified by washing with ethanol twice. After drying, it is recrystallized in 0.1 M HCl at 90° C. The yellow-orange product cis-diamminedichloridoplatinum(II) crystallizes out upon cooling, is centrifuged off, washed twice with ethanol and then dried.

Synthesis of cis,cis,trans-diamminedichloridodihydroxidoplatinum(IV) (cisplatinOH). Modified according to a synthesis known from the literature, 100 mg of cisplatin are suspended in 5 mL of water and an excess of 30% $H_2O_2$ (0.6 mL) is added. The mixture is stirred with stirring for 6 h at 70° C. and then overnight at room temperature. A color change from yellow-orange to light yellow takes place. The water is removed under vacuum, the light yellow product cis,cis,trans-diamminedichloridodihydroxidoplatinum(IV) is purified by washing twice with ethanol and then dried.

Embodiment 7: $[Ba]^{2+}{}_2[cisPt(AEP)_2]^{4-}$

The inorganic-organic hybrid $[Ba]^{2+}{}_2[cisPt(AEP)_2]^{4-}$ (AEP: aminoethyl phosphate) is prepared by mixing two solutions. Solution 1 contains $BaCl_2 \times 2H_2O$ (34 mg) in demineralized water (5.0 ml). Solution 2 contains potassium cis-dichloridodiaminoethylphosphatoplatinate(II) ($K_4[cisPt(AEP)_2]^{4-}$, 50.0 mg) in demineralized water (50 ml). Solution 2 was heated to 50° C. and stirred powerfully (about 1000 min$^{-1}$). Solution 1 was then injected quickly with a syringe with intensive stirring. After stirring for two minutes, the dark brown solid is separated off by centrifugation (15 min at 22,500 min$^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[Ba]^{2+}{}_2[cisPt(AEP)_2]^{4-}$, which contains $Ba^{2+}$ as an inorganic cation and the cytostatic anion $[cisPt(AEP)_2]^{4-}$, is obtained as amorphous nanoparticles with a diameter of about 30 nm.

For the preparation of potassium cis-dichloridodiaminoethylphosphatoplatinate(II) ($K_4[cisPt(AEP)_2]^{4-}$, 50 mg of $K_2PtCl_4$ and 34 mg of aminoethyl phosphate (AEP) are dissolved in 10 mL water and the pH value is set to 7-10 using NaOH. The solution is heated to 50° C. for 60 min. Here, a color change from light orange to dark brown takes place. The brown product ($K_4[cisPt(AEP)_2]^{4-}$ is then air-dried.

Embodiment 8: $[ZrO]^{2+}{}_2[(cisPt(AEP)_2)_{0.995}(DUT)_{0.005}]^{4-}$

The inorganic-organic hybrid $[ZrO]^{2+}{}_2[(cisPt(AEP)_2)_{0.995}(DUT)_{0.005}]^{4-}$ (AEP: aminoethyl phosphate) is prepared by mixing two solutions. Solution 1 contains $ZrOCl_2 \times 8H_2O$ (52 mg) in demineralized water (5.0 ml). Solution 2 contains potassium cis-dichloridodiaminoethylphosphatoplatinate(II) ($K_4[cisPt(AEP)_2]^{4-}$, 50.0 mg) as well as the near infrared emitting dye-modified nucleoside triphosphate DY-647-dUTP ($H_4(DUT)$, 1.0 mg, Dyomics) in demineralized water (50 ml). Solution 2 was heated to 50° C. and stirred powerfully (about 1000 min$^{-1}$). Solution 1 was then injected quickly with a syringe with intensive stirring. After stirring for two minutes, the brown solid is separated off by centrifugation (15 min at 22,500 min$^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[ZrO]^{2+}{}_2[(cisPt(AEP)_2)_{0.995}(DUT)_{0.005}]^{4-}$, which contains $[ZrO]^{2+}$ as an inorganic cation, the cytostatic anion $[cisPt(AEP)_2]^{4-}$ and the infrared-emitting fluorescence dye anion $[DUT]^{4-}$, is obtained as amorphous nanoparticles with a diameter of about 30 nm.

For the preparation of potassium cis-dichloridodiaminoethylphosphatoplatinate(II) ($K_4[cisPt(AEP)_2]^{4-}$, 50 mg of $K_2PtCl_4$ and 34 mg of aminoethyl phosphate (AEP) are dissolved in 10 mL water and the pH value is set to 7-10 using NaOH. The solution is heated to 50° C. for 60 min. Here, a color change from light orange to dark brown takes place. The brown product ($K_4[cisPt(AEP)_2]^{4-}$ is then air-dried.

Embodiment 9: $[ZrO]^{2+}{}_2[(cisPt(AEP)_2)_{0.5}(AlPCS_4)_{0.5}]^{4-}$

The inorganic-organic hybrid $[ZrO]^{2+}{}_2[(cisPt(AEP)_2)_{0.5}(AlPCS_4)_{0.5}]^{4-}$ (AEP: aminoethyl phosphate) is prepared by mixing two solutions. Solution 1 contains $ZrOCl_2 \times 8H_2O$ (52 mg) in demineralized water (5.0 ml). Solution 2 contains potassium cis-dichloridodiaminoethylphosphatoplatinate(II) ($K_4[cisPt(AEP)_2]^{4-}$, 50.0 mg) and aluminum(III)chloride phthalocyanine tetrasulfonate ($H_4(AlPCS_4)$, 72 mg) in demineralized water (50 ml). Solution 2 was heated to 50° C. and stirred powerfully (about 1000 min$^{-1}$). Solution 1 was then injected quickly with a syringe with intensive stirring. After stirring for two minutes, the dark brown solid is separated off by centrifugation (15 min at 22,500 min$^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 µm) in advance prior to use. The inorganic-organic hybrid $[ZrO]^{2+}{}_2[(cisPt(AEP)_2)_{0.5}(AlPCS_4)_{0.5}]^{4-}$, which contains $[ZrO]^{2+}$ as an inorganic cation, the cytostatic anion $[cisPt(AEP)_2]^{4-}$ and the photo-active and red-emitting active ingredient anion $[AlPCS_4]^{4-}$, is obtained as amorphous nanoparticles with a diameter of about 40 nm.

For the preparation of potassium cis-dichloridodiaminoethylphosphatoplatinate(II) ($K_4[cisPt(AEP)_2]^{4-}$, 50 mg of $K_2PtCl_4$ and 34 mg of aminoethyl phosphate (AEP) are dissolved in 10 mL water and the pH value is set to 7-10 using NaOH. The solution is heated to 50° C. for 60 min. Here, a color change from light orange to dark brown takes place. The brown product ($K_4[cisPt(AEP)_2]^{4-}$ is then air-dried.

Embodiment 10: $[ZrO]_2^{2+}[(Pt_2(POP)_4)_{0.5}(cisPt(AEP)_2)_{0.5}]^{4-}$

The inorganic-organic hybrid $[ZrO]2^{2+}[(Pt_2(POP)_4)_{0.5}(cisPt(AEP)_2)_{0.5}]^{4-}$ (POP: pyrophosphate, AEP: aminoethyl phosphate) is prepared by mixing two solutions. Solution 1 contains $ZrOCl_2 \times 8H_2O$ (52 mg) in demineralized water (5.0 ml). Solution 2 contains potassium pyrophosphatoplatinate (II) ($K_4[Pt_2(POP)_4]$, 80.0 mg) and potassium cis-dichloridodiaminoethylphosphatoplatinate(II) ($K_4[cisPt(AEP)_2]^{4-}$, 25.0 mg) in demineralized water (50 ml). Solution 2 was heated to 50° C. and stirred powerfully (about 1000 min$^{-1}$). Solution 1 was then injected quickly with a syringe with intensive stirring. After stirring for two minutes, the yellow solid is separated off by centrifugation (15 min at 22,500 min$^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[ZrO]2^{2+}[(Pt_2(POP)_4)_{0.5}(cisPt(AEP)_2)_{0.5}]^{4-}$, which contains $[ZrO]^{2+}$ as an inorganic cation, the cytostatic and green-emitting anion $[Pt_2(POP)_4]^{4-}$ and the cytostatic anion $[cisPt(AEP)_2]^{4-}$, is obtained as amorphous nanoparticles with a diameter of about 40 nm.

Potassium pyrophosphatoplatinate ($K_4[Pt_2(POP)_4]$) is produced according to a synthesis procedure known from the literature.

For the preparation of potassium cis-dichloridodiaminoethylphosphatoplatinate(II) ($K_4[cisPt(AEP)_2]^{4-}$, 50 mg of $K_2PtCl_4$ and 34 mg of aminoethyl phosphate (AEP) are dissolved in 10 mL water and the pH value is set to 7-10 using NaOH. The solution is heated to 50° C. for 60 min. Here, a color change from light orange to dark brown takes place. The brown product ($K_4[cisPt(AEP)_2]^{4-}$ is then air-dried.

Embodiment 11: $[ZrO]^{2+}_2[(cisPt(AEP)_2)^{4-}_{0.5}(BMP)^{2-}_{1.0}]^{4-}$

The inorganic-organic hybrid $[ZrO]^{2+}_2[(cisPt(AEP)_2)^{4-}_{0.5}(BMP)^{2-}_{1.0}]^{4-}$ (AEP: aminoethyl phosphate) is prepared by mixing two solutions. Solution 1 contains $ZrOCl_2 \times 8H_2O$ (52 mg) in demineralized water (5.0 ml). Solution 2 contains potassium cis-dichloridodiaminoethylphosphatoplatinate(II) ($K_4[cisPt(AEP)_2]^{4-}$, 50.0 mg) and sodium betamethasone phosphate ($Na_2(BMP)$, 129 mg) in demineralized water (50 ml). Solution 2 was heated to 50° C. and stirred powerfully (about 1000 min$^{-1}$). Solution 1 was then injected quickly with a syringe with intensive stirring. After stirring for two minutes, the dark brown solid is separated off by centrifugation (15 min at 22,500 min-1). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[ZrO]^{2+}_2[(cisPt(AEP)_2)^{4-}_{0.5}(BMP)^{2-}_{1.0}]^{4-}$, which contains $[ZrO]^{2+}$ as an inorganic cation, the cytostatic anion $[cisPt(AEP)_2]^{4-}$ and the glucocorticoid anion $[BMP]^{2-}$, is obtained as amorphous nanoparticles with a diameter of about 50 nm.

Embodiment 12: $[ZrO]^{2+}_2[(cisPt(AEP)_2)_{0.5}(FdUMP)_{1.0}]^{4-}$

The inorganic-organic hybrid $[ZrO]^{2+}_2[(cisPt(AEP)_2)_{0.5}(FdUMP)_{1.0}]^{4-}$ (AEP: aminoethyl phosphate) is prepared by mixing two solutions. Solution 1 contains $ZrOCl_2 \times 8H_2O$ (52 mg) in demineralized water (5.0 ml). Solution 2 contains potassium cis-dichloridodiaminoethylphosphatoplatinate(II) ($K_4[cisPt(AEP)_2]^{4-}$, 50.0 mg) and sodium-5'-fluoro-2'-deoxyuridine-5'-monophosphate ($Na_2(FdUMP)$, 82 mg) in demineralized water (50 ml). Solution 2 was heated to 50° C. and stirred powerfully (about 1000 min-1). Solution 1 was then injected quickly with a syringe with intensive stirring. After stirring for two minutes, the dark brown solid is separated off by centrifugation (15 min at 22,500 min$^{-1}$). The nanoparticles are resuspended twice in demineralized water (25 ml) and centrifuged again to remove any remaining salts. Finally, stable suspensions are obtained by resuspending the nanoparticles in HEPES buffer (12 ml, 30 mmol/l, pH=7.4). Alternatively, the centrifugate is resuspended in demineralized water (3.1 ml). A solution of dextran 40 (3 ml, 1.6 mg/ml $H_2O$) is subsequently dripped into this suspension with stirring. Alternatively, the nanoparticles can be redispersed in demineralized water only. In all cases, the demineralized water used is made free of dust and germs using a sterile syringe filter (PA, 0.20 μm) in advance prior to use. The inorganic-organic hybrid $[ZrO]^{2+}_2[(cisPt(AEP)_2)_{0.5}(FdUMP)_{1.0}]^{4-}$, which contains $[ZrO]^{2+}$ as an inorganic cation and the cytostatic anions $[cisPt(AEP)_2]^{4-}$ and $[FdUMP]^{2-}$, is obtained as amorphous nanoparticles with a diameter of about 40 nm.

The invention claimed is:

1. Inorganic-organic hybrid compound for use in medicine, made up as ionic compounds from an inorganic metal cation selected from $Ba^{2+}$, $[ZrO]^{2+}$, $[HfO]^{2+}$, $[GdO]^+$, $[Gd(OH)]^{2+}$, $[LaO]^+$, $[La(OH)]^{2+}$ or $Ag^+$, and an organic platinum-containing anion selected from $[Pt_2(POP)_4]^{4-}$ (POP: pyrophosphate), $[cisPt(AEP)_2]^{4-}$ (AEP: aminoethyl phosphate), or $[cisPt(PAA)_2]^{4-}$ (PAA: phosphonoacetate), wherein the compound has a molar solubility of $\leq 10^{-2}$ mol/l in water and a particle diameter in the range from 1 to 100 nm.

2. Inorganic-organic hybrid compound for use in medicine according to claim 1, which further comprises a fluorescence dye anion and/or an active ingredient anion, which each carry a phosphate, phosphonate, sulfate, sulfonate, carbonate or carboxylate group as a functional group.

3. Inorganic-organic hybrid compound for use in medicine according to claim 2, wherein the organic fluorescence dye anion is derived from fluorescence dyes selected from the group consisting of 1,1'-diethyl-2,2'-cyanine iodide, 1,2-diphenylacetylene, 1,4-diphenylbutadiene, 1,6-diphenylhexatriene, 2,5-diphenyloxazole, 2-methylbenzoxazole, 4',6-diamidino-2-phenylindole (DAPI), 4-(dicyanomethylene)-2-methyl-6-(p-dimethylaminostyryl)-4H-pyrane (DCM), 4-dimethylamino-4'-nitrostilbene, 5,10,15-triphenylcorrole, 5,10,15-tris (pentafluorophenyl)corrole, 5,10-diarylchlorin, 5,10-diarylcopper chlorin, 5,10-diarylcopper oxochlorin, 5,10-diarylmagnesium oxochlorin, 5,10-diaryloxochlorin, 5,10-diarylzinc chlorin, 5,10-diarylzinc oxochlorin, 7-benzylamino-4-nitrobenz-2-oxa-1,3-diazole, 7-methoxycoumarin-4-acetic acid, 9,10-bis(phenylethynyl)anthracene, 9,10-diphenylanthracene, acridine orange, acridine yellow, adenine, anthracene, anthraquinone, auramine O, azobenzene, Bacteriochlorophyll A, benzoquinone, beta-carotene, bilirubin, biliverdin dimethyl ester, bis(5-mesyldipyrrinato)zinc, bis(5-phenyldipyrrinato)zinc, boron subphtalocyanine chloride, chlorin E6, chlorophyll A, chlorophyll B, cis-stilbene, coumarin and derivatives thereof, cresyl violet perchlorate, cryptocyanine, crystal violet, cytosine, dansylglycine, diprotonated-tetraphenylporphyrin, eosin and derivatives thereof, ethyl-(p-dimethylamino)benzoate, ferrocene, fluorescein and derivatives thereof, methylfluorescein, resorufin, amaranth, aluminum (III)-phthalocyanine chloride, tetrasulfonic acid, trypan blue, guanine, hematine, histidine, Hoechst 33258, indocarbocyanine and derivatives thereof, Lucifer yellow CH, magnesium octaethylporphyrin, magnesium phthalocyanine, magnesium tetramesitylporphyrin, magnesium tetraphenylporphyrin, malachite green, merocyanine, N,N'-difluoroboryl-1,9-dimethyl-5-(4-iodophenyl)-dipyrrin, N,N'-difluoroboryl-1,9-dimethyl-5-[(4-(2-trimethylsilylethynyl)phenyl]dipyrrin, N,N'-difluoroboryl-1,9-dimethyl-5-phenydipyrrin, tetraphenylporphyrin, naphthalene, Nile Blue, Nile Red, octaethylporphyrin, oxacarbocyanine and derivatives thereof, oxazine and derivatives thereof, p-quarterphenyl, p-terphenyl, perylene and derivatives thereof, phenol, phenylalanine, phenyldipyrrin, pheophorbide, phthalocyanine, pinacyanol iodide, piroxicam, porphine, proflavine, protoporphyrin-IX-dimethyl ester, pyrene, pyropheophorbide and derivatives thereof, pyrrole, quinine, rhodamine and derivatives thereof, riboflavin, Bengal red, squarylium dye III, TBP-beta-octa(COOBu)-Fb, TBP-beta-octa(COOBu)-Pd, TBP-beta-octa(COOBu)-Zn, TBP-meso-tetraphenyl-beta-octa(COOMe)-Fb, TBP-meso-tetraphenyl-beta-octa(COOMe)-Pd, TBP-meso-tetraphenyl-beta-octa(COOMe)-Zn, TCPH-meso-tetra(4-COOMe-phenyl)-Fb, TCPH-meso-tetra(4-COOMe-phenyl)-Pd, TCPH-meso-tetra(4-COOMe-phenyl)-Zn, tetra-t-butylazaporphine, tetra-t-butylnaphthalocyanine, tetrakis(2,6-dichlorophenyl)porphyrin, tetrakis(o-aminophenyl)porphyrin, tetramesityl porphyrin, tetraphenylporphyrin, tetraphenylsapphyrin, thiacarbocyanine and derivatives thereof, thymine, trans-stilbene, tris(2,2'-bipyridyl)ruthenium(II), tryptophan, tyrosine, uracil, vitamin B12, zinc octaethylporphyrin, phthalocyanine and derivatives thereof, porphyrin and derivatives thereof, including tetra(o-amidophosphonophenyl)porphyrin, and umbelliferone, wherein the organic fluorescence dyes, which as such do not have a phosphate, phosphonate, sulfate, sulfonate, carbonate or carboxylate group, are modified with at least one of these functional groups.

4. Inorganic-organic hybrid compound for use in medicine according to claim 2, wherein the active ingredient anion is derived from acetaminophen phosphate, betamethasone phosphate, dexamethasone phosphate, uridine monophosphate, 5'-fluoro-2'-deoxyuridine-5'-monophosphate (FdUMP), methylprednisolone phosphate, triamcinolone phosphate, estrone phosphate, testosterone phosphate, estramustine phosphate, codeine phosphate, clindamycin phosphate, thiamine pyrophosphate, thiamine phosphate, aracytidine monophosphate, cyclic-3'5'-adenosine monophosphate, vidarabine phosphate, 9-[9-(phosphonomethoxy)ethoxy]adenine, fospropofol, fosphenytoin, phosphoryloxymethyloxymethylphenytoin, phosphoryloxymethylphenylbutazone, phosphoryloxymethyloxymethylphenylbutazone, phosphoryloxymethylphenindione, phosphoryloxymethyloxymethylphenindione, N-phosphonooxymethylcinnarizine, N-phosphonooxymethylloxapine, N-phosphonooxymethylamiodarone, alendronate, canrenoate, doxycycline hydrate, doxorubicin hydrochloride, aztreonam, tigemonam, D-glucosamine-6-sulphate, colistin methanesulphate, cefsulodin, fosamprenavir, tenofovir, adefovir, combretastatin A-4 phosphate, folic acid, fosphenytoin, sodium 2-mercaptoethanesulfonate (MESNA), fosfomycin, glyphosate, glufosinate, zoledronate, aminotrimethylene phosphonic acid, diethylenetriamine penta(methylene phosphonic acid), ethylenediamine tetra(methylene phosphonic acid), fosbretabulin, α-tocopherol phosphate, VAPOL hydrogenphosphate, pyridoxal-5'-phosphate-6-(2'-naphthylazo-6'-nitro-4',8'-disulfonate), (11bR)-2,6-di-9-phenanthrenyl-4-hydroxy-dinaphtho[2,1-d:1',2'-f][1,3,2]dioxaphosphepine-4-oxide, 8-bromo-cyclic adenosine diphosphate ribose, phytic acid, glucose-6-phosphate or other phosphoric acid esters of sugars or naturally occurring and synthetic nucleotides including adenosine monophosphate (AMP), adenosine diphosphate (ADP), adenosine triphosphate (ATP), guanosine monophosphate (GMP), guanosine diphosphate (GDP), guanosine triphosphate (GTP), cytidine monophosphate (CMP), cytidine diphosphate (CDP), cytidine triphosphate (CTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxycytidine monophosphate (dCMP), deoxycytidine diphosphate (dCDP), deoxycytidine triphosphate (dCTP), deoxythymidine monophosphate (dTMP), deoxythymidine diphosphate (dTDP) deoxythymidin triphosphate (dTTP).

5. Inorganic-organic hybrid compound for use in medicine according to claim 2, wherein the additionally incorporated organic active ingredient anion is derived from acetaminophen phosphate, betamethasone phosphate, dexamethasone phosphate, 5'-fluoro-2'-deoxyuridine-5'-monophosphate (FdUMP), methyl prednisolone phosphate, triamcinolone phosphate, estrone phosphate, estramustine phosphate, codeine phosphate, clindamycin phosphate, fospropofol, alendronate, canrenoate, doxycycline hydrate, doxorubicin, aztreonam, tigemonam, cefsulodin, fosamprenavir, tenofovir, adefovir, folic acid, fosfomycin, α-tocopherol phosphate or glucose-6-phosphate.

6. Inorganic-organic hybrid compound for use in medicine according to claim 1, which is in an X-ray amorphous form.

7. Inorganic-organic hybrid compound for use in medicine according to claim 1, wherein it is free from corresponding matrices or encapsulations surrounding it and free from any phospholipid matrices or encapsulations.

8. Inorganic-organic hybrid compound for use in medicine according to claim 1, which is further functionalized with one or more tumor-specific ligands.

9. A method for producing an inorganic-organic hybrid compound according to claim 1, comprising the steps of:
  (a) providing a solution of a platinum-containing anion compound selected from $[Pt_2(POP)_4]^{4-}$ (POP: pyrophosphate), $[cisPt(AEP)_2]^{4-}$ (AEP: aminoethyl phosphate), or $[cisPt(PAA)_2]^{4-}$ (PAA: phosphonoacetate),
  (b) providing a solution of a soluble metal salt containing metal cations selected from $Ba^{2+}$, $[ZrO]^{2+}$, $[HfO]^{2+}$, $[GdO]^+$, $[Gd(OH)]^{2+}$, $[LaO]^+$, $[La(OH)]^{2+}$, or $Ag^+$,
  (c) combining the two solutions by stirring in order to precipitate the hybrid compound, and
  (d) isolating and/or purifying the precipitated hybrid compound.

* * * * *